US00PP18562P2

(12) United States Plant Patent
Radler

(10) Patent No.: US PP18,562 P2
(45) Date of Patent: Mar. 4, 2008

(54) SHRUB ROSE PLANT NAMED 'RADSUNNY'

(50) Latin Name: *Rosa hybrida*
Varietal Denomination: Radsunny

(75) Inventor: William J. Radler, Greenfield, WI (US)

(73) Assignee: CP Delaware, Inc., Wilmington, DE (US)

( * ) Notice: Subject to any disclaimer, the term of this patent is extended or adjusted under 35 U.S.C. 154(b) by 8 days.

(21) Appl. No.: 11/495,552

(22) Filed: Jul. 31, 2006

(51) Int. Cl.
*A01H 5/00* (2006.01)

(52) U.S. Cl. ..... Plt./104

(58) Field of Classification Search ..... Plt./104
See application file for complete search history.

*Primary Examiner*—Kent Bell
*Assistant Examiner*—S. B. McCormick-Ewoldt
(74) *Attorney, Agent, or Firm*—Buchanan Ingersoll & Rooney PC

(57) ABSTRACT

A new and distinct variety of shrub rose plant is provided which forms in abundance on a nearly continuous basis attractive single blossoms that are yellow in coloration. The vegetation is vigorous and strong and the growth habit is round and bushy. Attractive ornamental satiny green foliage is formed. Excellent disease resistance with respect to blackspot is displayed. The new variety is particularly well suited for growing as distinctive ornamentation in the landscape.

3 Drawing Sheets

Botanical/commercial classification: *Rosa hybrida*/Shrub Rose Plant.
Varietal denomination: cv. Radsunny.

SUMMARY OF THE INVENTION

The new variety of *Rosa hybrida* shrub rose plant of the present invention was created at Greenfield, Wis., U.S.A., by artificial pollination wherein two parents were crossed which previously had been studied in the hope that they would contribute the desired characteristics. The female parent (i.e., the seed parent) was the 'Radbrite' variety (U.S. Plant Pat. No. 17,391). The male parent (i.e., the pollen parent) of the new variety was the 'Radsweet' variety (non-patented in the United States). The 'Radbrite' variety is being marketed under the Brite Eyes trademark. The parentage of the new variety can be summarized as follows:

'Radbrite'×'Radsweet'.

The seeds resulting from the above pollination were sown and small plants were obtained which were physically and biologically different from each other. Selective study resulted in the identification of a single plant of the new variety.

It was found that the new shrub rose plant of the present invention possesses the following combination of characteristics:

(a) abundantly forms attractive single blossoms that are yellow in coloration, (b) exhibits a round and bushy growth habit, (c) forms vigorous vegetation, (d) forms attractive ornamental green foliage with a satiny finish, and (e) exhibits excellent resistance to blackspot.

A new rose variety is provided having yellow blossoms combined with substantially continuous blooming and blackspot resistance. The blooming cycle is believed to be one of the longest observed to date for a rose plant.

The new variety well meets the needs of the horticultural industry. It can be grown to advantage as ornamentation in parks, gardens, public areas, and in residential settings. The new variety is particularly well suited for providing attractive ornamentation in the landscape. The yellow blossoms contrast nicely with the satiny green foliage.

The new variety of the present invention also can be readily distinguished from its ancestors. More specifically, the 'Radbrite' variety displays an upright and climbing growth habit and forms salmon-pink blossoms with a yellow eye, and the 'Radsweet' variety forms light pink blossoms that commonly fade to near white. The flowers of the new variety display a mild spicy fragrance, whereas the flowers of each parent display no fragrance. The sweetbriar fragrance of the foliage of the 'Radsunny' variety is stronger than that of both parental varieties. The 'Radsunny' flowers commonly possess more petals than the 'Radsweet' variety, but not as many as the 'Radbrite' variety. Also, the foliage color of the 'Radsunny' variety tends to be lighter than that of the parental varieties. The disease resistance and hardiness are similar in all three varieties.

Additionally, the new 'Radsunny' variety can be readily distinguished from the 'Radrazz' variety (U.S. Plant Pat. No. 11,836) and the 'Meipotal' variety (U.S. Plant Pat. No. 8,841 upon an inspection of the blossom color. The blossoms of the 'Radrazz' variety are cherry red in coloration, and those of the 'Meipotal' variety are pink with white eyes.

The characteristics of the new variety have been found at Waso, Calif., U.S.A., and near West Grove, Pa., U.S.A., to be homogeneous and stable and to be strictly transmissible by asexual propagation such as budding, grafting, and the rooting of cuttings from one generation to another. The new variety reproduces true to type by such asexual propagation.

The new variety has been named 'Radsunny'.

BRIEF DESCRIPTION OF THE PHOTOGRAPHS

The accompanying photographs show, as nearly true as it is reasonably possible to make the same in color illustrations of this character, typical flowering plants of the new variety. The illustrated rose plants of the new variety were approximately two years of age and were observed during June while growing outdoors on their own roots near West Grove, Pa., U.S.A.

DETAILED DESCRIPTION

Figure 1:
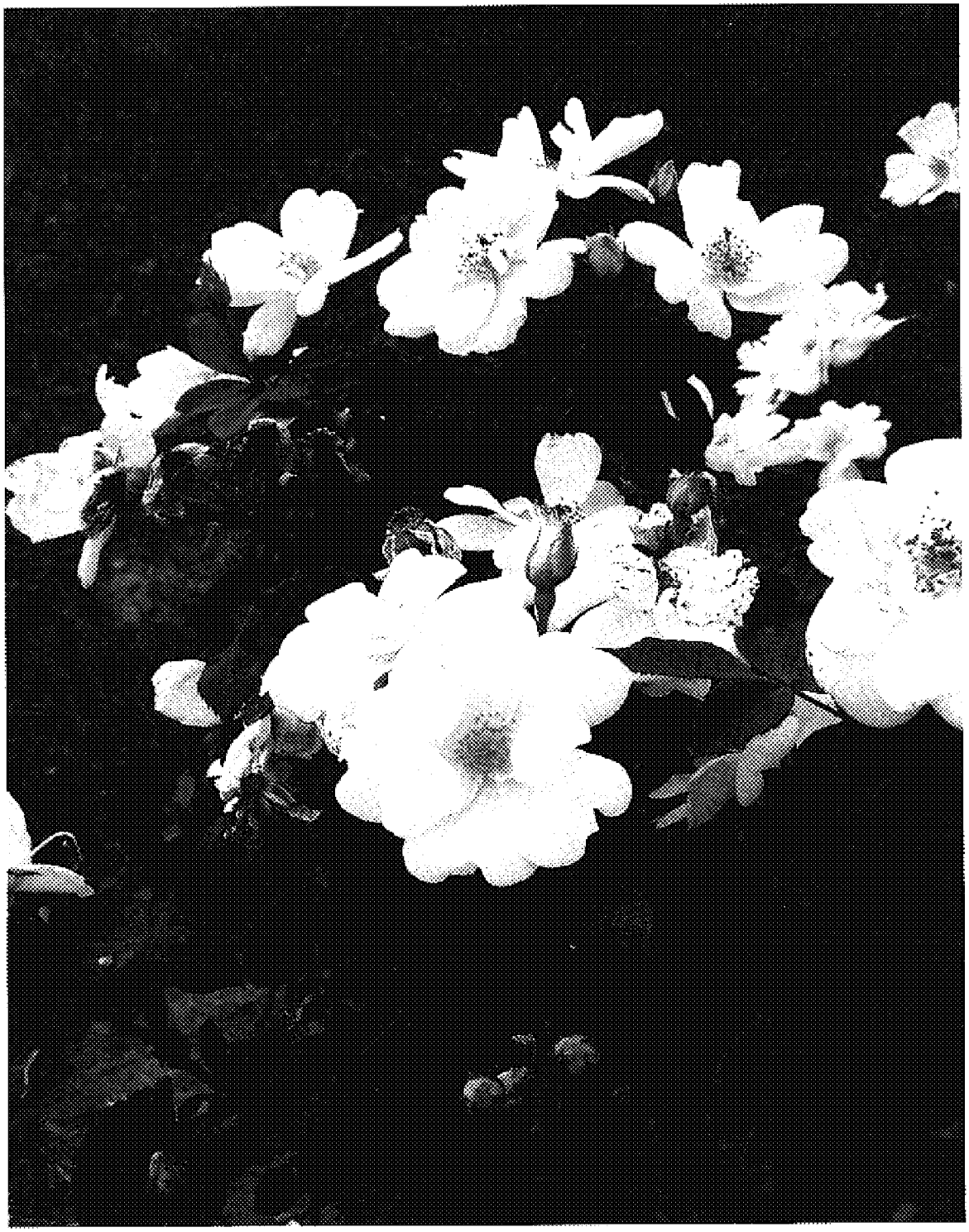
FIG. 1 shows the buds, blossoms, and foliage of the 'Radsunny' variety. Many of the blossoms are at the final stage of maturity.
Figure 2:
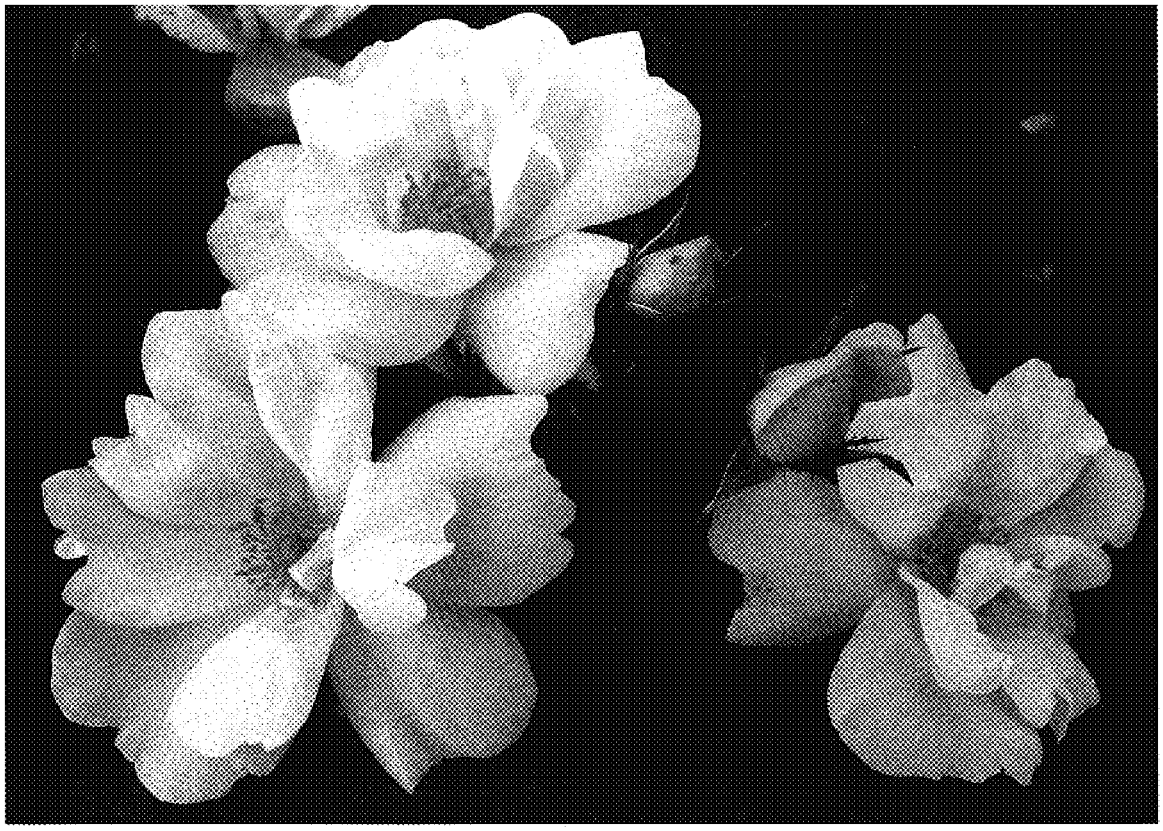
FIG. 2 shows a closer view of the buds and blossoms of the 'Radsunny' variety. The blossoms are at an intermediate stage of maturity.
Figure 3:
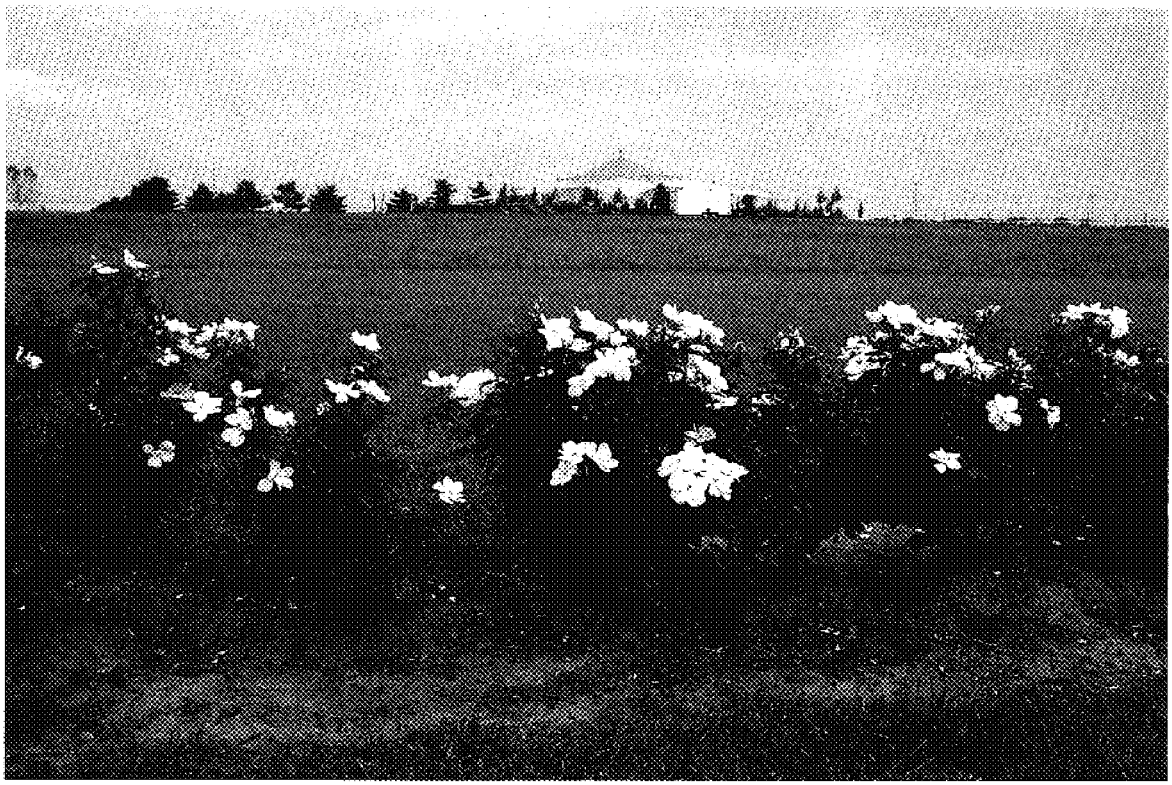
FIG. 3 shows a row of blossoming plants of the 'Radsunny' variety wherein the typical round and bushy growth habit is illustrated. Many of the blossoms are at a final stage of maturity.

The chart used in the identification of colors is that of The Royal Horticultural Society (R.H.S. Colour Chart), London, England. The description is based on the observation of two-year-old specimens of the new variety during June while growing outdoors on their own roots near West Grove, Pa., U.S.A.

Class: Landscape Shrub.

Plant:

*Height.*—Approximately 3 feet on average at the end of the growing season. The mature height is approximately 4 feet on average.

*Width.*—Approximately 3 feet on average at the end of one growing season. The mature width is approximately the same.

*Habit.*—Round and bushy.

Branches:

*Color.*—Young stems: near Yellow-Green Group 144B with some highlights of Red Group 53A. Adult wood: Yellow-Green Group 144A suffused with Red-Purple Group 184A.

*Thorns.*—Size: approximately 1 to 1.5 cm in length on average with some smaller bristles/prickles near the peduncle. Quantity: sparse, and commonly less than one per inch on average. Color: Greyed-Purple Group 184B.

Leaves:

*Size.*—Approximately 9 to 11 cm in length.

*Stipules.*—Parallel with auricle facing outward.

*Petioles.*—Upper surface: Yellow-Green Group 144B with highlights of Greyed-Purple Group 184A, and commonly bear some prickles. Under surface: Yellow-Green Group 14B with highlights of Greyed-Purple Group 184A.

*Leaflets.*—Number: 3, 5, and 7. Length: approximately 4.5 cm on average for a terminal leaflet. Width: approximately 2.5 cm on average for a terminal leaflet. Shape: ovate with a rounded base and an acuminate tip. Margins: serrulate. Texture: smooth and satiny. Overall appearance: very dense, leathery, and medium green in coloration, with a satiny finish. Color (young foliage): Upper surface: Green Group 138A. Under surface: Green Group 138B. Color (adult foliage): Upper surface: Green Group 137A. Under surface: Green Group 138B.

Inflorescence:

*Number of flowers.*—Commonly approximately 4 to 5 blooms on average in a cluster.

*Peduncle.*—Medium green, Yellow-Green Group 146D, with some prickles, and approximately 5 cm in length on average.

*Sepals.*—Inner surface: with some pubescence and commonly between Green Group 138B and 138C in coloration. Outer surface: Yellow-Green Group 146B with some areas of Yellow-Green Group 144C at the base. Number: five.

*Buds.*—Shape: generally slender (as illustrated). Length: approximately 2 cm on average as the calyx breaks. Size: small to medium. Color (upper surface): commonly between Yellow Group 13A and 13B. Color (under surface): commonly between Yellow Group 13B and 13C.

*Flower.*—Form: single. Shape: informal. Diameter: approximately 6 to 7 cm. on average when fully open. Color (when opening begins): Upper surface: near Yellow Group 13A. Under surface: commonly between Yellow Group 13B and 13C. Color (when blooming): Upper surface: between Yellow Group 11A and 11B. Under surface: between Yellow Group 11A and 11B. Color (at end of blooming): Upper surface: between Yellow Group 11C and 11D. Under surface: Yellow Group 11C with highlights of Yellow Group 11D at the center. Fragrance: mild spicy. Petal form: wedge-shaped with a curled apex. Petal length: approximately 3 cm on average. Petal width: approximately 2.5 cm on average. Petal number: approximately 10 on average. Texture: the upper surfaces are satiny. Lasting quality: blossoms commonly last approximately one week on the plant depending upon environmental conditions, and approximately one week when cut and placed in a vase. Petal drop: very good, the petals drop cleanly and freely. Stamen number: approximately 70 on average, and regularly arranged about the pistils. Anthers: Greyed-Yellow Group 162B in coloration. Filaments: Red Group 48D in coloration. Pistils: separate and free, and commonly number approximately 30 on average. Stigmas: Yellow Group 13C in coloration. Styles: Red Group 45B in coloration. Hips: generally obovate in shape, commonly approximately 3.5 cm in length on average, commonly approximately 2.5 cm in diameter on average, and near Orange Group 24B in coloration. Seeds: generally oblong, commonly approximately 7 mm in length, commonly approximately 5 mm in diameter, and near Yellow-Orange Group 19C in coloration. Receptacle: achenes are present on the bottom wall.

Development:

*Vegetation.*—Vigorous and strong.

*Blossoming.*—Abundant and substantially continuous during the growing season.

*Resistance to diseases.*—Excellent with respect to blackspot and rust when compared to other commercial varieties under comparable growing conditions near West Grove, Pa., U.S.A.

*Formation of hips/seeds.*—Sparse.

I claim:

1. A new and distinct shrub rose plant characterized by the following combination of characteristics:

(a) abundantly forms attractive single blossoms that are yellow in coloration, (b) exhibits round and bushy growth habit, (c) forms vigorous vegetation, (d) forms attractive ornamental green foliage with a satiny finish, and (e) exhibits excellent resistance to blackspot;

substantially as herein shown and described.

* * * * *